United States Patent [19]

Sell

[11] 4,030,579

[45] June 21, 1977

[54] LINEAL LOCK FOR X-RAY APPARATUS

[75] Inventor: Leslie James Sell, Orangeville, Canada

[73] Assignee: Picker X-Ray Mfg. Limited, Bramalea, Canada

[22] Filed: Mar. 26, 1975

[21] Appl. No.: 562,141

[52] U.S. Cl. .............................. 188/171; 188/67; 188/165

[51] Int. Cl.² ..................................... B60T 13/04

[58] Field of Search .................. 250/320, 448, 525; 188/44, 67, 88.84, 163, 165, 170, 171

[56] References Cited

UNITED STATES PATENTS

| | | | |
|---|---|---|---|
| 1,031,637 | 7/1912 | Fischer | 188/67 UX |
| 1,989,235 | 1/1935 | Kimball | 188/171 X |
| 2,224,147 | 12/1940 | Ehlers | 188/67 X |
| 2,401,256 | 5/1946 | Lear | 188/171 X |
| 2,673,627 | 3/1954 | Stava et al. | 188/165 |
| 3,096,854 | 7/1963 | Price et al. | 188/171 X |
| 3,198,293 | 8/1965 | Mathews | 188/171 X |

Primary Examiner—Duane A. Reger

Attorney, Agent, or Firm—Watts, Hoffmann, Fisher & Heinke Co.

[57] ABSTRACT

Relative translational movement between a pair of X-ray apparatus components is selectively arrested by a bidirectional lineal lock structure including an elongated locking rod carried by one of the components and a locking unit carried by the other component. The locking unit is movable along the locking rod and includes two sets of balls which selectively engage the peripheral surface of the rod. Two clamping systems normally wedge the balls into clamping engagement with the peripheral surface, preventing relative, component movement. A pair of electromagnets are operative, when energized, to bias the clamping systems toward release positions to permit relative componet movement. Either of the electromagnets may be selectively energized to permit unidirectional relative movement between the components. An energizing circuit is provided for briefly reversing the polarity of the electromagnets immediately before they are de-energized, to faciliate re-establishment of the clamping engagement.

23 Claims, 4 Drawing Figures

LINEAL LOCK FOR X-RAY APPARATUS

RELATED REFERENCE TO RELATED PATENTS AND APPLICATION

MOUNT FOR CEILING SUPPORTED TUBE, Ser. No. 418,057, filed Nov. 21, 1973 by W. H. Amor, Jr., et al., here the "Mechanical Lock Patent."

X-RAY APPARATUS AND CONTROL, U.S. Pat. No. 2,823,315, issued Feb. 11, 1958 to R. J. Stava, et al., as a division of ELECTROMAGNETIC LOCK FOR X-RAY APPARATUS, U.S. Pat. No. 2,673,627, issued Mar. 30, 1954 to R. J. Stava, et al., here the "Electromagnetic Lock Patents."

LOCKING DEVICE FOR X-RAY APPARATUS. U.S. Pat. No. 2,673,626, issued Mar. 30, 1954 to E. J. Bastin, here the "Unidirectional Lock Patent."

BACKGROUND OF THE INVENTION

1. Field of the Invention

The present invention relates to X-ray apparatus, and more particularly, to an electromagnetically operated bidirectional lineal lock structure for selectively arresting relative translational movement between two X-ray apparatus components.

2. Prior Art

In modern X-ray rooms, an X-ray apparatus includes a number of relatively movable components for supporting and relatively positioning a patient, an X-ray source, and an imaging device. The movable components lend versatility to the apparatus and enable its use for various diagnostic and treatment purposes, with techniques which vary widely depending on the prescribed type of examination or treatment.

When the movable components of the X-ray apparatus have been positioned properly for a medical procedure, it is desirable to lock the components in place to prevent their relative movement. A locking system employed for this purpose should permit the components to be locked precisely where they have been positioned, and should not require their movement to other positions before the locks will engage.

Frictional locks, both mechanical and electrical, have been used in X-ray apparatus. Mechanically operated locking systems have suffered a number of drawbacks. One of the major drawbacks of mechanically operated locking systems is that they are slow and difficult to operate.

The referenced Electromagnetic Lock Patents describe a locking system which is a substantial improvement over prior mechanical systems. Relatively movable components are provided with electromagnetic pucks which, when energized, arrest relative component movement. This locking system self-adjusts for wear, is relatively simple and inexpensive, and requires minimal maintenance. The locking system described by these patents enables a large number of relatively movable components to be positioned for use and to be simultaneously and accurately locked in position. This type of electromagnetic locking system has achieved wide acceptance in the industry.

A problem not addressed by the Electromagnetic Lock Patents is that of arresting relative component movement in the event of a power failure. The system must be energized to arrest relative component movement. Another problem not addressed in these Electromagnetic Lock Patents is that of providing a unidirectional release capability.

The referenced unidirectional Lock Patent describes an electromagnetic lock which is operable somewhat like a mechanical ratchet and pawl system to prevent relative movement of two X-ray apparatus components in one direction, while enabling relative movement in the opposite direction. A disadvantage of this system is that is uses a motion preventing lock which must be electrically energized to restrict relative component movement. A further disadvantage is that some relative component movement in the undesired direction must take place initially before the lock is energized to prohibit further undesired movement.

Another problem with prior locking systems used in X-ray apparatus is that the components which are locked in place may be subject to forces which will unexpectedly cause their relative movement when the locking system releases. The referenced Mechanical Lock Patent describes one mechanical approach to solving this problem between two relative rotatable components. A manual release button is connected to a release dog by a compression coil spring. When the button is depressed, the forces transmitted to the dog will be insufficient to release the dog if the forces on the rotationally locked components have not been relieved by an operator. By this arrangement, one cannot accidentally release the dog by depressing the button at any time other than when the forces tending to rotate the components have been relieved.

Table top X-ray tables employ table tops which are movable longitudinally and laterally relative to a supporting pedestal to position a patient for an X-ray procedure. Where electrically energized locking devices are employed to retain the table top in selected longitudinal and lateral positions, it is desirable for these devices to normally arrest component movement and to release only when energized. While it is desirable to arrest movement if, for example, a power failure occurs, electromagnetic locks have not had this capability.

It is also desirable for the locks to resist release if forces above a predetermined level are applied to the components at the time of release. For example, if a person is leaning against the table top and accidentally trips a lock release, it is desirable for the locking devices to retain the table top in position rather than to release and permit unexpected and undesired table top movement. Prior locking systems have lacked this ability to restrain accidental movement.

SUMMARY OF THE INVENTION

The present invention overcomes the foregoing and other drawbacks of the prior art by providing a novel and improved lineal lock structure for arresting the relative translational movement of X-ray apparatus components.

A locking system is provided which permits two X-ray apparatus components to be securely locked at any selected position within a range of relative component movement. The locking system is normally engaged and releases only when actuated. The locking system can be unidirectionally or bidirectionally released to permit unidirectional or bidirectional relative component movement.

A locking rod is secured to one of two movable components. The locking rod parallels the path of relative translational movement between the components. A locking unit is secured to the other component. A locking unit is slidably journaled on the locking rod. When the components move relative to each other along the path, the locking unit slides along the locking rod.

The locking unit includes an electromagnetically-released clamping system for selectively grasping the locking rod to arrest relative component movement. The clamping system is normally engaged and releases only when electrically energized and only when forces above a predetermined level and tending to cause relative component movement have been relieved.

The locking unit includes a tubular housing that surrounds the locking rod. A pair of electromagnet coils are positioned in opposite end regions of the housing. Two axially movable armatures are mounted in the housing between the coils. Each of the armatures coacts with a set of hardened steel balls which selectively engage the peripheral surface of the locking rod.

Each armature is movable between a clamp position and a release position. When the armatures are in their clamp positions, the balls are wedged tightly into contact with the peripheral surface of the locking rod and arrest relative component movement. When the armatures are in the release positions, the balls loosely receive the locking rod and do not inhibit relative component movement.

The armatures are spring biased toward the clamp positions. The coils are operative, when energized, to attract the armatures toward their release positions and overcome the spring bias.

If external forces tending to cause relative component movement are applied while the locking system is locked, such forces will cause the clamping system to wedge the balls more forcefully into contact with the locking rod. If such forces are in effect when the coils are energized, the attraction force produced by the coils will be insufficient to release the locking unit. Once the external forces are relieved, the locking unit will release.

One of the armatures and its associated balls normally engages the locking rod arresting relative component movement in one direction axial of the locking rod. The other of the armatures and its associated balls normally engages the locking rod arresting relative component movement in the opposite direction axial of the locking rod. If only one of the coils is energized, unidirectional relative component movement is permitted by the locking system. If both of the coils are energized, bidirectional relative component movement is permitted.

If the relatively movable components are connected for translation by a guide rod and lineal bearing connection, the lineal locking unit can operate on the guide rod and does not require the provision of a separate locking rod. The locking unit can be a self-contained assembly separate from the lineal bearings, or can be constructed to include the lineal bearing assemblies in a common housing.

In the preferred embodiment, the locking system of the present invention is employed between guide-rod-and-bearing connected X-ray apparatus components where the locking rod is separate from the guide rod, and the locking unit is separate from the lineal bearings. This arrangement facilitates repair and replacement of the locking unit without disassembling the connection between the movable components.

Accordingly a general object of the present invention is to provide a novel and improved lineal lock.

Other objects and a fuller understanding of the invention may be had by referring to the following description and claims taken in conjunction with the accompanying drawings.

DESCRIPTION OF THE PREFERRED EMBODIMENT

Figure 1:
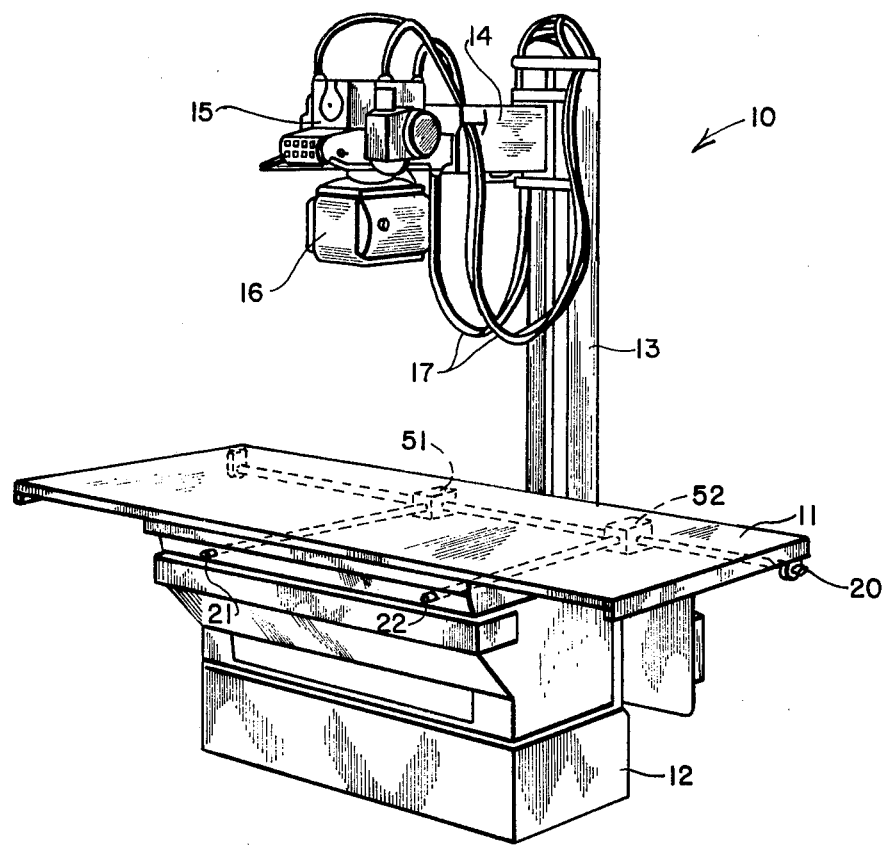
FIG. 1 is a perspective view of an X-ray apparatus embodying the present invention.

Referring to FIG. 1, an X-ray apparatus is indicated generally by the numeral 10. The apparatus 10 includes a table top 11 supported on a pedestal 12. A tower 13 is carried by the pedestal 12. A carriage 14 is supported on the tower 13 for vertical movement. An X-ray source 15 including a collimator 16 is supported on the carriage 14. Suitable power cables 17 connect with the X-ray source 15 for energizing the source 15. An X-ray film support (not shown) called a Bucky tray is provided beneath the table top 11 to receive X-radiation which has been emitted from the source 15 and has passed through portions of a patient positioned on the table top 11.

The table top 11 is movably supported on the pedestal 12 to facilitate positioning of a patient beneath the X-ray source 15. An arrangement of guide rods and bearings provides a movable connection between the table top 11 and the pedestal, and permits the table top 11 to be translated selectively in longitudinal and lateral directions relative to the pedestal 12.

A number of bearings, not shown, are interposed between the table top 11 and the pedestal 12 to permit the table top 11 to be moved freely in a horizontal plane relative to the pedestal 12. A longitudinal guide rod 20 and a pair of lateral guide rods 21, 22 are provided beneath the table top 11 to guide the movement of the table top 11 relative to the pedestal 12. The guide rods 20, 21, 22 extend with their axes in a common horizontal plane, as shown in dotted lines in FIG. 1.

Figure 2:
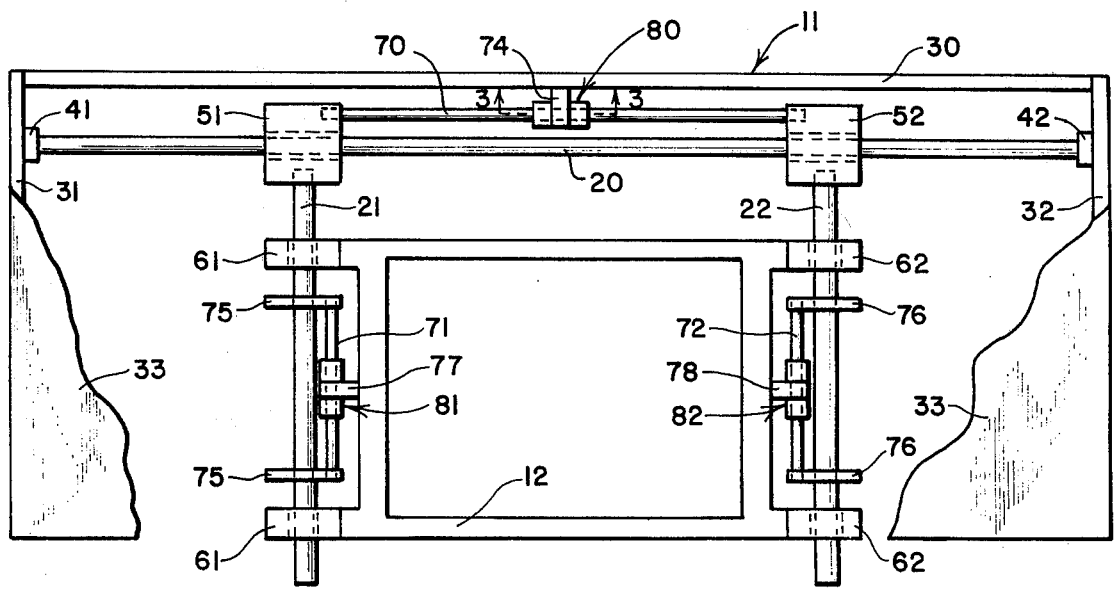
FIG. 2 is an enlarged top plan view of the X-ray apparatus with some portions broken away and other portions removed to illustrate the locking system arrangement.

Referring to FIG. 2, the table top 11 has a three-sided horizontal framework including a rear beam 30 and a pair of side beams 31, 32. A top plate 33 is supported by the beams 30, 31, 32.

A pair of brackets 41, 42 are secured to the side beams 31, 32. The brackets 41, 42 depend beneath the table top 11 and rigidly connect with opposite end regions of the longitudinal guide rod 20.

A pair of bearing block assemblies 51, 52 are carried by the lateral guide rods 21, 22. The bearing block assemblies 51, 52 slidably receive the longitudinal guide rod 20. Two pairs of bearing block assemblies 61, 62 are carried by the pedestal 12. The bearing block assemblies 61, 62 slidably receive the lateral guide rods 21, 22.

A locking rod 70 extends between the longitudinal bearing block assemblies 51, 52. The locking rod 70 parallels the longitudinal guide rod 20. An electromagnetically operated lineal lock assembly 80 slidably receives the locking rod 70. A bracket 74 secures the lock assembly 80 to the back beam 30.

A pair of locking rods 71, 72 parallel the lateral guide rods 21, 22. Two pairs of brackets 75, 76 secure opposite ends of the locking rods 71, 72 to the guide rods 21, 22. A pair of electromagnetically operated lineal lock assemblies 81, 82 slidably receive the locking rods 71, 72. A pair of brackets 77, 78 secure the lock assemblies 81, 82 to the pedestal 12.

The lock assemblies 80, 81, 82 are of identical construction. The locking rods 70, 71, 72 are of uniform diameter and are formed from surface hardened steel.

When the lock assemblies 80, 81, 82 are de-energized, they grasp the locking rods 70, 71, 72 and arrest horizontal movement of the table top 11 relative to the pedestal 12. When the lock assembly 80 is energized, it releases its grip on the locking rod 70 and permits the table top 11 to be moved longitudinally relative to the pedestal 12. When the lock assemblies 81, 82 are energized, they release their grip on the locking rods 71, 72 and permit the table top 11 to be moved laterally relative to the pedestal 12. When all of the lock assemblies 80, 81, 82 are concurrently energized, the table top 11 can be moved freely in a horizontal plane relative to the pedestal 12.

Figure 3:
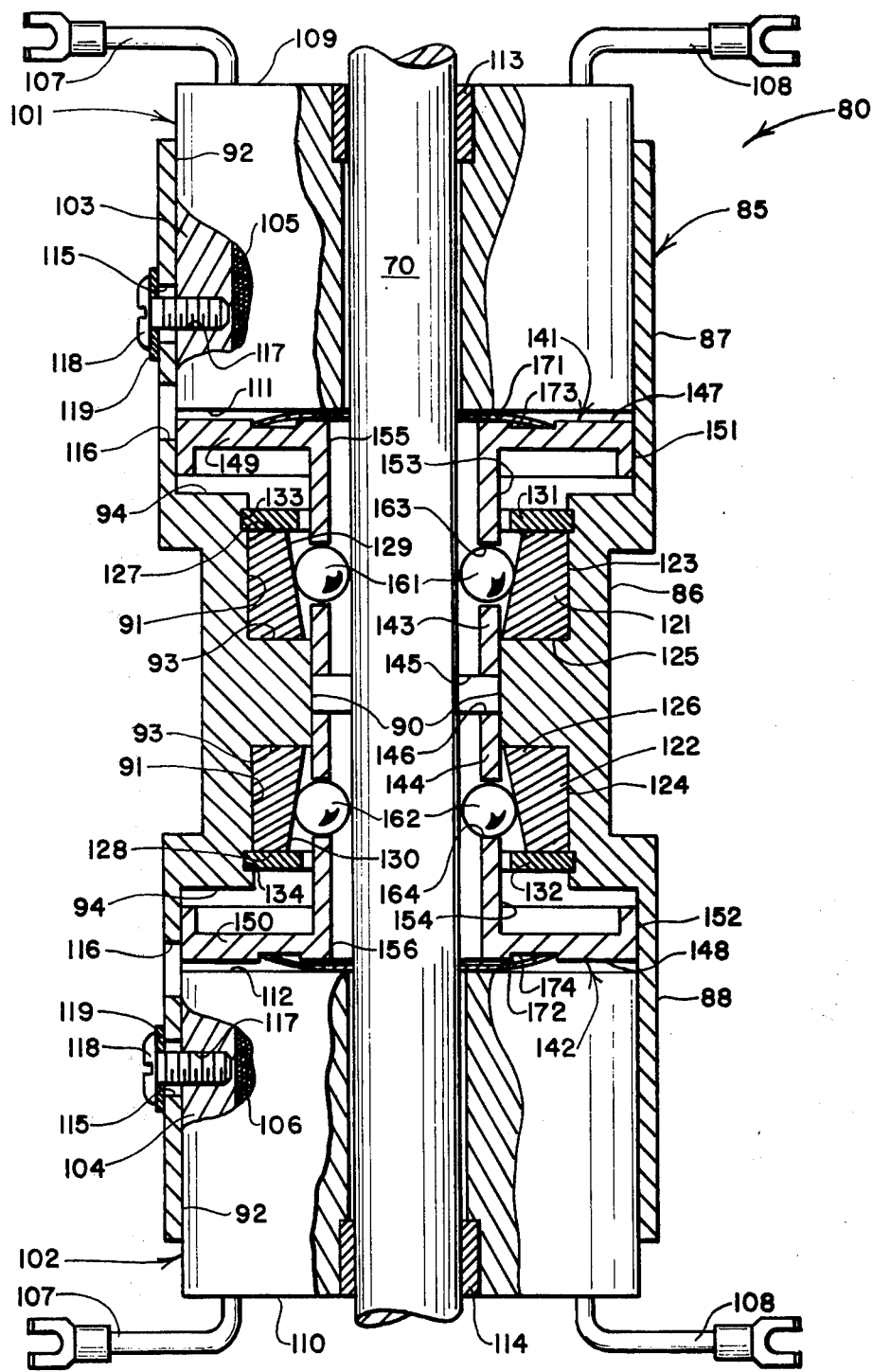
FIG. 3 is an enlarged cross-sectional view of a locking unit as seen from the plane indicated by the line 3—3 in FIG. 2; and, FIG. 4 is a schematic electrical circuit diagram showing a circuit which energizes a locking units.

Referring to FIG. 3, the electromagnetically operated lineal lock assembly 80, includes an assembly housing 85. The assembly housing 85 is cylindrical and has a central region 86 of lesser diameter than its end regions 87, 88.

A stepped bore extends axially through the assembly housing 85. The bore has a central region 90 of relatively small diameter, spaced, intermediate regions 91 of a larger diameter, and further spaced outermost regions 92 of still larger diameter. Radially extending annular shoulders 93 connect the central and intermediate regions 90, 91. Radially extending annular shoulders 94 connect the intermediate and outermost regions 91, 92.

A pair of electromagnetic coil assemblies 101, 102 are respectively positioned in the outermost regions 92. The coil assemblies 101, 102 include annular coil housings 103, 104 which support coil windings 105, 106. Two pairs of conductors 107, 108 respectively connect with opposite ends of the coil windings 105, 106.

The coil assemblies 101, 102 have outer end surfaces 109, 110 and inner end surfaces 111, 112. The outer end surfaces 109, 110 are located beyond the ends of the assembly housing 85. The inner end surfaces 111, 112 are spaced from the shoulders 94. A pair of bushings 113, 114 are pressed into the coil housings 103, 104 adjacent the outer end surfaces 109, 110. The bushings 113, 114 slidably receive the locking rod 70.

Two pairs of slots 115, 116 are formed through the assembly housing 85 in communication with outermost regions 92. The slots 115, 116 are elongated in directions axial of the locking rod 70. The slots 115 align with threaded holes 117 formed in the coil housings 103, 104. Threaded fasteners 118 extend through flat washers 119, through the slots 115, and are threaded into the holes 117 to secure the coil assemblies 101, 102 to the assembly housing 85. The slots 115 permit limited axial adjustment of the coil assemblies 101, 102 relative to the housing 85. The slots 116 permit access to the inner end surfaces 111, 112, as will be explained, to facilitate proper positioning of the coil assemblies 101, 102.

A pair of hardened annular bushings 121, 122 are positioned in the intermediate housing regions 91. The bushings 121, 122 have circular peripheral surfaces 123, 124 which fit loosely within the circular walls of the intermediate regions 91. The bushings 121, 122 have inner end walls 125, 126 in engagement with the shoulders 93, and outer end walls 127, 128 spaced inwardly from the shoulders 94.

A pair of retainer rings 131, 132 hold the bushings 121, 122 in place in the intermediate regions 91. A pair of grooves 133, 134 are formed in the cylindrical walls of the intermediate regions 91 adjacent the bushing end surfaces 127, 128. The retainer rings 131, 132 are conventional spring steel snap rings which are positioned in the grooves 133, 134 and engage the bushing end surfaces 127, 128 to hold the bushings 121, 122 in place.

The bushings 121, 122 have tapered bores 129, 130. The bores 129, 130 converge toward the peripheral surface of the locking rod 70 as they extend from the outer end surfaces 127, 128 to the inner end surfaces 125, 126.

A pair of axially movable locking armatures 141, 142 are movably carried in the housing 85. The armatures 141, 142 have cylindrical, tubular stems 143, 144 extending between inner end surfaces 145, 146 and outer end surfaces 147, 148. Radially outwardly extending flanges 149, 150 are formed near the outer end regions of the stems 143, 144.

The flanges 149, 150 have circular peripheral surfaces 151, 152 that fit loosely within the housing walls 92. The stems 143, 144 have circular peripheral surfaces 153, 154 which extend loosely through the bushing bores 129, 130 and slip-fit within the housing wall 90. The stems 143 144 have central bores 155, 156. The locking rod 170 extends axially through the bores 155, 156 without contacting the stems 143, 144.

A plurality of hardened balls 161, 162 are interposed between the hardened locking rod 70 and the hardened bushings 121, 122. A plurality of holes 163, 164 are formed through the stems 143, 144. The balls 161, 162 are rotatably positioned in the holes 163, 164 and are movable axially of the locking rod 70 with the armatures 141, 142.

The armatures 141, 142 are axially movable between positions where the balls 161, 162 loosely receive the locking rod 70, and where the balls 161, 162 are tightly clamped against the locking rod 70. In the position of FIG. 3, spaces of about 0.25 to about 0.38 millimeter in width are provided between the coil inner end surfaces 111, 112 and the armature outer end surfaces 147, 148. When the armatures 141, 142 are in the position of FIG. 3, the balls 161, 162 are wedged snugly between the tapered bore walls 129, 130 and the peripheral surface of the locking rod 70. When the armatures 141, 142 move closer to the coil inner end surfaces 111, 112, the balls 161, 162 are no longer wedged against the locking rod 70, and the rod 70 can move axially relative to the lineal lock assembly 80.

A pair of spring steel washers 171, 172 are interposed between the coil assemblies 101, 102 and the armatures 141, 142. The washers 171, 172 are conventional Belleville washers and have the characteristic curved Bellville cross-section with peripheral regions biased out of the plane of central regions of the washers 171, 172. A pair of annular grooves 173, 174 are formed in the armature outer end surfaces 147, 148. The peripheral regions of the washers 171, 172 extend into the grooves 173, 174. The washers 171, 172 bias the armatures 141, 142 inwardly to the position of FIG. 3 where the balls 161, 162 are wedged into firm gripping engagement with the locking rod 70.

When the electromagnetic coil assemblies 101, 102 are energized, by supplying a potential difference across the conductors 107, 108, the armatures 141, 142 are attracted by the magnetic fields produced by the coil windings 105, 106. If the locking unit 80 and the locking rod 70 are not being subjected to external forces in excess of a predetermined level which tend to cause relative movement of the table top 11 and the pedestal 12, the magnetic fields produced by the coil windings 105, 106 will have sufficient strength to move the armatures 141, 142 outwardly toward the coil assemblies 101, 102. The outward movement of the armatures moves the balls 161, 162 so their grip on the rod 70 is released and movement of the table top 11 relative to the pedestal 12 may occur.

If external forces in excess of a predetermined level are tending to move the table top 11 longitudinally when the locking unit 80 is clamping the locking rod 70, such forces will wedge one of the sets of balls 161, 162 into tight clamping engagement with the locking rod 70. If such forces continue when the coils 105, 106 are energized, the armature 141, 142 associated with the more tightly clamped set of balls will not move under the influence of its associated magnetic field, but will stay in its clamped position until the external forces are relieved.

The slots 116 formed through the housing 85 provide access to the spaces between the coil inner end surfaces 111, 112 and the armature outer end surfaces 147, 148. The slots 116 permit the insertion of feeler gages between the end surfaces 111, 112 and 147, 148 to measure and set the gaps between these end surfaces. The width of the gaps between the end surfaces 111, 112 and 147, 148 is adjusted by loosening the fasteners 118, axially moving the coil assemblies 101, 102 relative to the housing 85, and retightening the fasteners 118.

Figure 4:
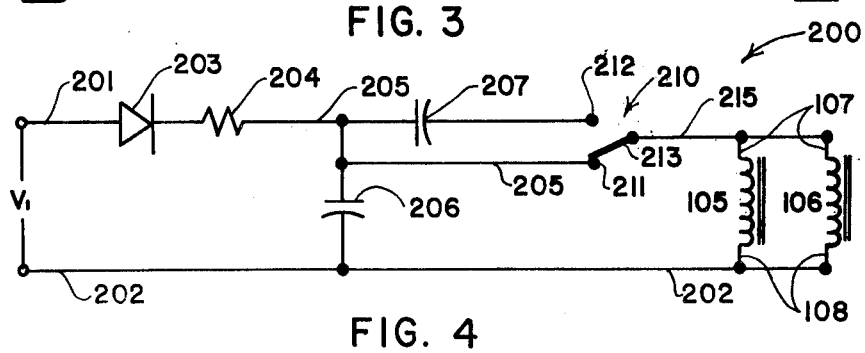

The locking units 80, 81, 82 are preferably energized through identical circuits, one of which is shown at 200 in FIG. 4. While the circuit in FIG. 4 is arranged to concurrently energize both of the coils 105, 106, it will be obvious that these coils can be provided with separate actuating circuits for selectively unidirectionally restricting the relative movement between the locking units 80, 81, 82 and the locking rods 70, 71, 72.

A feature of the circuit shown in FIG. 4 is that when the electromagnets 109, 110, in the locking units 80, 81, 82 are de-energized, the circuit briefly reverses the polarity of the electromagnets 109, 110 to repel the armatures 141, 142 and re-establish clamping engagement. While the locking units of the present invention will operate without such a reversing circuit, it is desirable to use such a circuit in order to positively assure that the units 80, 81, 82 lock after each energization.

Referring to FIG. 4, the circuit 200 includes a pair of line conductors 201, 202. The conductors 201, 202 are connected across a source of electrical energy (not shown) at a potential difference of V1. The potential difference V1 is co-pulsating DC voltage such as is obtained by passing an AC current through a full wave rectifier. A blocking diode 203 and a current limiting resistor 204 are connected in series between the line conductor 201 and an intermediate conductor 205. The diode 203 has its anode connected to the source V1 and its cathode connected to the resistor 204. The line conductor 202 connects directly with the coil conductors 108.

A pair of capacitors 206, 207 each have one terminal connected to the intermediate conductor 205. The other terminal of the capacitor 206 connects with the line conductor 202.

A double pole single throw switch 210 selectively connects the coil conductors 107 with the intermediate conductor 205 and with the other terminal of the capacitor 207. The switch 210 has fixed contacts 211, 212, and a movable contact 213. The fixed contact 211 connects with the intermediate conductor 205. The fixed contact 212 connects with the capacitor 207. The movable contact 213 connects through a conductor 215 with the coil conductors 107.

Operation of the circuit 200 is best understood by examining the circuit 200 at a time after the movable switch contact 213 has engaged the fixed contact 212 and the circuit 200 is in steady state. At such time, both of the capacitors 206, 207 are charged to the voltage V1, and no current is flowing through the coils 105, 106. The coils 105, 106 are accordingly de-energized, and the locking unit 80 is clamped in engagement with the locking rod 70.

When the movable switch contact 213 is moved into engagement with the fixed contact 211 a current flow is established through the coils 105, 106. As the coils 105, 106 are energized, the capacitor 206 discharges to a value V2, where V2 is less than V1. A voltage difference of V2 also appears across the coils 105, 106, once steady state is achieved. The coils 105, 106 are accordingly energized to release the locking unit 80.

When the movable switch contact 213 is returned to engagement with the fixed contact 212, the capacitor 207 (which has previously been charged to the voltage V1) is connected in series with the coils 105, 106. The charged capacitors 206, 207 and the energized coils 105, 106 cooperate to cause a transitory voltage pulse of V2 - V1 to appear across the coils 105, 106. This pulse momentarily reverses the polarity of the magnetic fields produced by the coils 105, 106.

The effect of the field reversal is to cause the magnetized armatures 141, 142 to be repelled toward each other. As the armatures 141, 142 move rapidly toward each other, the balls 161, 162 are brought rapidly into firm clamping engagement with the locking rod 70. The field reversal augments the biasing action of the spring steel washers 171, 172 and "sets" the balls 161, 162 firmly against the locking rod 70.

Once the transitory V2 - V1 pulse has passed through the coils 105, 106, steady state returns to the circuit 200 and the capacitors recharge to the voltage V1.

Although the invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. In an X-ray apparatus including a pair of translatably movable components, a lineal lock system interposed between the components for selectively arresting their relative movement, comprising:

a. an elongated member carried by one of the components and defining a longitudinally extending surface;

b. the other of the components normally engaging said surface to arrest relative component movement; c. an electrically energizable locking means connected to a first of the components; the locking means being energizable in a first condition to permit unidirectional relative component movement and in a second condition to permit bidirectional component movement.

2. The X-ray apparatus of claim 1 wherein said other component includes:
   a. mechanical means biased into clamping engagement with said surface; and,
   b. release means operable to selectively permit said unidirectional and bidirectional movement.

3. The X-ray apparatus of claim 2 wherein said release means includes electromagnets operable when energized in the first condition selectively to permit unidirectional relative component movement, and when energized in the second condition to permit bidirectional relative component movement.

4. The X-ray apparatus of claim 3 wherein a circuit means is connected to electromagnets, the circuit means being operable momentarily to reverse the polarity of the magnetic field being created by one of said electromagnets prior to de-energization of said one electromagnet whereby the reversed magnet field repels to urge relative component movement toward the normally engaged condition.

5. An electromagnetically operated lineal lock interposed between two relatively movable components of an X-ray apparatus, comprising:
   a. an elongated member connected to one of the components and having a longitudinally extending surface;
   b. a locking unit connected to the other of the components and being movable longitudinally relative to said member in opposite directions;
   c. first electromagnetically operated clamping means forming part of said locking unit and being operable to engage said surface selectively to permit or arrest relative movement of the components in a first direction; and,
   d. second electromagnetically operated clamping means forming part of said locking unit and being operable to engage said surface selectively to permit or arrest relative movement of the components in a second direction.

6. The apparatus of claim 5 wherein each of said clamping means includes:
   a. a plurality of components movably carried in said housing structure for engaging said surface;
   b. wedging means interposed between said housing structure and said components for selectively wedging said components into clamping engagement with said surface;
   c. biasing means coupled to said wedging means for normally effecting such clamping engagement; and,
   d. electromagnetic means adapted for connection to a source of electrical energy and operable in response to such connection to counteract the biasing action of said biasing means.

7. The apparatus of claim 6 additionally including circuit means connected to said electromagnetic means, said circuit means being operatable momentarily to reverse the polarity of such magnetic field prior to de-energization of the electromagnetic means, whereby the reversed magnetic field exerts a momentary repulsion force on said wedging means to assist said biasing means in effecting such clamping engagement.

8. An electromagnetically operated lineal lock, comprising:
   a. an elongated member having a longitudinally extending surface;
   b. a locking unit movable longitudinally relative to said member in first and second opposite directions;
   c. first electromagnetically operated clamping means forming part of said locking unit and being operable to selectively permit and arrest relative movement in said first direction between said member and said unit;
   d. second electromagnetically operated clamping means forming part of said locking unit and being operable to selectively permit and arrest movement in said second direction between said member and said unit.

9. The apparatus of claim 8 wherein each of said clamping means includes:
   a. a plurality of components movably carried in said housing structure for engaging said surface;
   b. wedging means interposed between said housing structure and said components for selectively wedging said components into clamping engagement with said surface;
   c. biasing means coupled to said wedging means for normally effecting such clamping engagement; and,
   d. electromagnetic means adapted for connection to a source of electrical energy and operable in response to such connection to counteract the biasing action of said biasing means.

10. The apparatus of claim 9 additionally including circuit means connected to said electromagnetic means, said circuit means being operatable momentarily to reverse the polarity of such magnetic field prior to de-energization of the electromagnetic means, whereby the reversed magnetic field exerts a momentary repulsion force on said wedging means to assist said biasing means in effecting such clamping engagement.

11. An electromagnetically operated lineal lock interposed between two relatively movable support components of an X-ray apparatus, comprising:
   a. an elongated member connected to one of the components and having a peripheral surface;
   b. a locking unit connected to the other of said components, and being movable longitudinally of said member, said locking unit comprising:
      i. a tubular housing;
      ii. a pair of electromagnets positioned near opposite ends of said housing and having coils surrounding said members;
      iii. a pair of armatures movably carried within said housing between each electromagnets;
      iv. said armatures each having a portion which surrounds and extends axially of said members;
      v. a plurality of balls coactable with said portions and interposed between said tapered surfaces and said member;
      vi. biasing means biasing said armatures to positions where balls are clamped by said tapered surfaces into firm engagement with said peripheral surface of said member;

vii. said electromagnets being operative when energized by connection to a source of electrical energy to exert a biasing force on said armatures to move said armatures toward positions where such clamping engagement is relieved.

12. The apparatus of claim 11 wherein the biasing forces applied by said electromagnets is insufficient to move one of said armatures to release the clamping force of its associated balls when external forces tending to effect relative longitudinally movement of said unit and said member are applied to said unit and said member.

13. The apparatus of claim 12 wherein said biasing means is interposed between said electromagnets and said armatures.

14. The apparatus of claim 13 additionally including means for adjusting the position of said electromagnets longitudinally of said member relative to said housing.

15. The X-ray apparatus of claim 11 wherein a circuit means is connected to electromagnets, the circuit means being operable momentarily to reverse the polarity of the magnetic field being created by one of said electromagnets prior to de-energization of said one electromagnet whereby the reversed magnet field repels to urge relative component movement toward the normally engaged condition.

16. An electromagnetically operated lineal lock, comprising:
   a. an elongated member having a longitudinally extending surface;
   b. a locking unit movable longitudinally of said member and including;
      i. a housing;
      ii. a plurality of balls carried in said housing for engagement with said surface;
      iii. clamping means carried by said housing including a magnetically responsive clamping structure for retaining said balls and being movable between a clamped position where said balls are clamped against said surface to arrest relative movement between said member and said unit, and a released position where said balls permit relative movement;
      iv. biasing means for urging said structure toward the clamped position;
      v. Electromagnet means for producing a magnetic field sufficiently strong to urge said structure toward the released position except when substantial external longitudinal movement forces are being applied to said unit and said member.

17. An electromagnetically operated lineal lock, comprising:
   a. an elongated member having a longitudinally extending surface;
   b. a locking unit movable longitudinally of said member and including:
      i. a housing;
      ii. a plurality of balls carried in said housing for engagement with said surface;
      iii. clamping means carried by said housing including a clamping element movable between a clamped position where said balls are clamped against said surface to arrest relative movement between said member and said unit, and a released position where said balls permit relative movement;
      iv. biasing means for biasing said element toward the clamped position;
      v. the electromagnet adapted in response to electric energy to provide a magnetic field which urges said element toward the released position; and,
   c. circuit means connected to the electromagnet, the circuit means being operatable momentarily to reverse the polarity of the magnetic field created by the electromagnet prior to de-energization of said electromagent, whereby the reversed magnetic field repels the element and cooperates with the biasing means to move the element to the clamped position.

18. A lineal lock interposed between two relatively movable components of an X-ray apparatus, comprising:
   a. an elongated member having a longitudinally extending surface;
   b. a locking unit movable longitudinally of said member and including;
      i. a housing structure;
      ii. a plurality of components movably carried in said housing structure for engaging said surface;
      iii. wedging means interposed between said housing structure and said components for selectively wedging said components into clamping engagement with said surface;
      iv. biasing means coupled to said wedging means for normally effecting such clamping engagement; and,
   c. circuit means connected to the electromagnet, the circuit means being operatable momentarily to reverse the polarity of such magnetic field prior to de-energization of said electromagnet, whereby the reversed magnetic field exerts a momentary repulsion force on said wedging means to assist said biasing means in effecting clamping engagement.

19. In a X-ray apparatus of type including relatively movable support components, the improvement of an electromagnetically operated lineal lock for selectively arresting relative component movement, comprising:
   a. an elongated member connected to one of the components;
   b. a locking unit connected to the other of the components and including:
      i. a housing;
      ii. a plurality of balls carried in said housing for engagement with said member;
      iii. a clamping element carried by said housing and movable between a clamped position where said balls are clamped against said member to arrest relative movement, and a released position where said balls permit relative movement;
      iv. biasing means for biasing said element toward the clamped position;
      v. an electromagnet adapted when energized to provide a magnetic field biasing said clamping element toward the released position; and,
   c. circuit means for connecting the electromagnet to a source of energy, said circuit means being operatable momentarily to reverse the polarity of the magnetic field created by said electromagnet prior to the de-energization of the electromagnet, whereby the reversed magnetic field repels the element and cooperates with said biasing means to move said element to the clamped position.

20. An x-ray apparatus, comprising:
   a. a supporting structure;

b. a supported structure movably carried by the supporting structure;
c. a normally engaged locking system interposed between said structures to prevent their relative movement, and operative when electrically actuated to permit relative movement, said locking system including selectively releasing means operatable when actuated in a first condition to permit unidirectional relative movement of said structures, and when actuated in a secnd condition to permit bidirectional relative movement of 21. An X-ray apparatus, comprising:
a. a supporting structure;
b. a supported structure movably carried by the supporting structure;
c. a normally engaged locking system interposed between said structures to prevent their relative movement, and operative when electrically actuated to permit relative movement, said locking system including,
  i. an elongated member carried by one of said structures;
  ii. a locking unit carried by the other of said structures and movable into the other structure along said member when said structures move relative to each other;
  iii. said locking unit including clamping means biased into engagement with said member to normally prevent relative movement of said structures, said locking unit also including release means operable when actuated to oppose the biasing of said clamping means.

22. The X-ray apparatus of claim 21 wherein said release means includes electromagnet means operable when energized to oppose the biasing of said clamping means.

23. An electromagnetically operated lineal lock, comprising:
a. an elongated member having a longitudinally extending surface;
b. a locking unit movable longitudinally of said member and including;
  i. a housing;
  ii. a plurality of balls carried in said housing for engagement with said surface;
  iii. clamping means, carried by said housing, for retaining said balls for movement relative to said elongated member, said clamping means including a magnetically responsive element movable between a clamping position wherein said element transmits forces to wedge said balls against said surface to arrest relative movement between said member and said unit, and a relative positon wherein said element has transmitted forces to displace said balls from wedged engagement with said surface to enable relative movement of said member and said unit;
  iv. biasing means for urging said element toward the clamped position; and
  v. electromagnet means for producing a magnetic field sufficiently strong to urge said magnetic clamping element toward the released position except when external longitudinal movement forces are applied to said unit and said member.

* * * * *

UNITED STATES PATENT OFFICE
CERTIFICATE OF CORRECTION

Patent No. 4,030,579            Dated June 21, 1977

Inventor(s) Leslie James Sell

It is certified that error appears in the above-identified patent and that said Letters Patent are hereby corrected as shown below:

Col. 2, line 3, delete "unidirectional" substitute
-- Unidirectional --

Col. 2, line 9, after "that", delete "is" substitute -- it --

Col. 2, line 31, before "X-ray" delete "Table top"

Col. 6, line 63, delete "Belleville" substitute -- Bellville --

Col. 10, line 15, after "unit;" insert -- and, --

Col. 13, line 10, delete "secnd", substitute -- second --

Col. 13, line 11, after "of" insert -- said structures. --

Col. 14, line 18, before "position", delete "clamping" substitute -- clamped --

Col. 14, line 21, before "position", delete "relative" and substitute -- released --

Column 6, line 64, delete "Belville" should read -- Belleville --.

Signed and Sealed this

Twenty-ninth Day of November 1977

[SEAL]

Attest:

RUTH C. MASON      LUTRELLE F. PARKER
*Attesting Officer*      *Acting Commissioner of Patents and Trademarks*